United States Patent [19]

Jensen et al.

[11] Patent Number: 4,720,465
[45] Date of Patent: Jan. 19, 1988

[54] CENTRIFUGAL KINETIC AGGLUTINATION ASSAY

[75] Inventors: Mona D. Jensen, Hampstead, N.H.; Kwok K. Yeung, Malvern, Pa.; Pih-Kuei C. Huang, Lexington, Mass.; Brian B. Lentrichia, Mahway, N.J.; Robert J. Dummel, White Plains, N.Y.

[73] Assignee: Fisher Scientific Company, Pittsburgh, Pa.

[21] Appl. No.: 733,688

[22] Filed: May 14, 1985

[51] Int. Cl.[4] .............. G01N 33/557; G01N 33/543; G01N 33/551; G01N 33/546
[52] U.S. Cl. .................... 436/523; 436/517; 436/518; 436/524; 436/531; 436/534; 436/805
[58] Field of Search .............. 436/514, 517, 518, 524, 436/531, 534, 538, 805, 533, 523

[56] References Cited

U.S. PATENT DOCUMENTS

| | | | |
|---|---|---|---|
| 4,003,988 | 1/1977 | Hoff et al. | 436/534 |
| 4,202,665 | 5/1980 | Wenz et al. | 436/517 |
| 4,205,954 | 6/1980 | Babson | 436/517 |
| 4,305,721 | 12/1981 | Bernstein | 436/520 X |

OTHER PUBLICATIONS

Wenz, B. et al., Clin. Chem., 25, No. 9:1613–1616 (1979).

Primary Examiner—Robert J. Warden
Assistant Examiner—Jack Spiegel
Attorney, Agent, or Firm—Alan M. Doernberg

[57] ABSTRACT

A sample is mixed with a reagent containing stably suspended particles coated with a binding pair member complementary to or competitive with the target binding pair member. A centrifugal force applied during reaction is sufficient to change the concentration of particles at a locus relative to overall particle concentration. Light transmission or scattering is measured kinetically at the locus, especially in a microcentrifugal analyzer.

8 Claims, 4 Drawing Figures

CENTRIFUGAL KINETIC AGGLUTINATION ASSAY

BACKGROUND OF THE INVENTION

The present invention relates to agglutination assays, and especially to such assays which quantitate binding pair members in a sample through the use of a light transmission or scattering measurement.

Agglutination immunoassays are known wherein particles coated with an immuological binding pair member (antigen or antibody) agglutinate in the presence of active complementary binding pair members. In the simplest such immunoassays, the level of antigen in the sample affects the extent of agglutination of antibody-coated particles, with increased turbitity being caused by increased agglutination, as an indication of elevated levels of target antigen. In competitive agglutination immunoassays, a fixed amount of antibody in solution causes reduced levels of agglutination of antigen-coated particles as increased levels of target antigen compete for limited binding sites on the antibody. Conventionally, such agglutination is determined qualitatively by visual observation after a fixed reaction period, in some cases after rapid centrifugation at the conclusion of the reaction period to concentrate the agglutinated particles as in U.S. Pat. No. 4,373,931 to Takekawa (1983).

Quantitative analysis of agglutination by light transmission or scattering measurement has been proposed in a variety of patents: e.g., U.S. Pat. Nos. 4,118,192 to Sawai et al. (1978), 4,205,954 to Babson (1980) and 4,224,304 to Sawai et al. (1980). In these patents, a plurality of light transmittance measurements are taken over time; and the change in transmission, due to the change in optical density corresponding to agglutination of single particle into clusters, is used as an indication of the degree of agglutination. Such measurements rely upon a constant total particle concentration in the sample light path, with the local rearrangement of particles in clusters of two or more particles affecting light differently over time as a function of agglutination.

U.S. Pat. No. 4,202,665 to Wenz (1980) and Wenz et al., Clin. Chem. 25: 1613-1616 (1979) disclose a hemagglutination assay for hepatitis performed in a microcentrifugal analyzer. Rapid changes in absorbance due to centrifugation are observed (over a 90 second time frame in most cases); the slope of absorbance decline is increased by agglutination of the antibody-coated cells when antigen is present. Other types of particles, including polymers, are referred to.

BRIEF DESCRIPTION OF THE INVENTION

The present invention is based upon the conduct of an agglutination reaction in a centrifugal field under conditions wherein agglutinated particles migrate in the field as they form at a rate different from the migration of unagglutinated particles. While the invention is particularly applicable to agglutination immunoassays, it applies equally to assays wherein agglutination is caused by specific binding reactions other than that between antigens and antibodies.

Accordingly, the present invention includes a method for the determination of a target binding pair member in a sample which comprises:

(a) admixing the sample with a reagent containing stably suspended particles, the particles being coated with a member selected from the group consisting of binding pair members complementary to the target binding pair member and binding pair members competitive with the target binding pair member, the mixture further containing complementary binding pair member when the coated member is competitive;

(b) subjecting the mixture during reaction between binding pair members to a centrifugal force sufficient to differentially change the concentration of particles in the mixture at a locus relative to the total concentration of particles in the mixture, the rate of such change being a function of the degree of agglutination of the particles;

(c) measuring the light transmission or scattering at the locus at a plurality of points of time during reaction and application of centrifugal force; and (d) comparing the change in light measurement over time at the locus for the mixture containing sample with changes in light measurement over time at the locus from mixtures containing standard samples of known concentration of the target pair member.

DETAILED DESCRIPTION OF THE INVENTION

Figure 1:
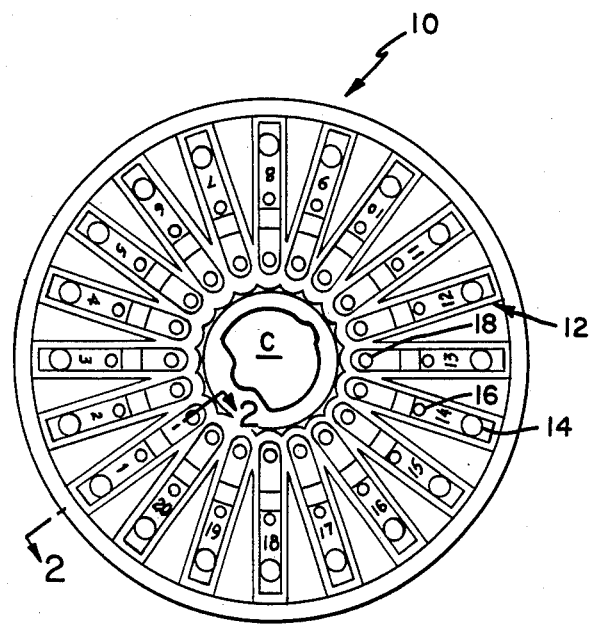
FIG. 1 is a top plan view of a rotor used in the present process.

The method of the present invention can be used to quantitate a variety of binding pair members in a variety of samples. It is particularly applicable to the quantitation of antibodies, antigens or haptens in biological samples such as whole blood, serum, plasma, spinal fluid, urine or the like. To the extent that such fluids naturally contain suspended particles (e.g., blood cells) it is preferred to remove or lyse such particles prior to the present test. Depending upon the expected concentration of the target binding pair member, it may be desirable either to dilute the sample prior to introduction into the present mixture or to add a diluent simultaneously or subsequently to the admixture of the sample with the reagent used in the present method. An exemplary target binding pair member which is not detected by immunological binding is nucleic acid, which, in the present invention, would be detected through the use of particles coated with complementary or competitive nucleic acid strands.

The particles used in the present invention are stably suspended in a liquid medium. By "stably" is meant that the particles will remain in suspension for at least an hour upon standing. Such particles, in a centrifugal field, will migrate outwardly only slowly, and then reach an equilibrium gradient. By contrast, the red cells used in U.S. Pat. No. 4,202,665 are, even in the absence of agglutination, unstable; they settle upon standing and migrate rapidly outward in a centrifugal field. While Wenz refers at col. 6, line 64—col. 7, line 6 to various other particulates, there is no appreciation of any advantages obtained by employing stable suspensions.

The particles used in one of the reagents of the method of the present invention can be conventional latex particles, and especially polystyrene latex particles of diameter about 0.05 to about 2.0 microns (about 50 to 200 nm), preferably of about 0.1 to about 0.8 microns. Such particles are suspended in aqeuous medium (generally containing buffers, salts, surfactants and the like) and coated with a binding pair member. For direct assays, antibodies against the target binding pair member can be used, either of the conventional polyclonal or monoclonal antibodies raised against the target antigen (or against an antigen analog of the target hapten). The concentration, method of coating, addition of inert coatings (such as albumin) and other preparative aspects of the coated particles can be as is conventional in qualitative agglutination immunoassays such as are sold by a variety of venders and used and observed in non-automated kits. Exemplary references to such coated particles are the following U.S. Pat. Nos. 4,092,114 to Buck (1978), 3,088,875 to Fisk (1963). As is conventional in such assays, the concentration of binding pair member on the particles, the concentration of particles in the reagent and the relative proportions of reagent and sample are adjusted in combination in such fashion that changes in target antigen concentration in the sample over the expected range produce significant (and preferably linear) changes in degree of agglutination of the mixture.

In similar fashion, for competitive agglutination immunoassays, the particles are coated with a binding pair member (e.g., antigen if the target is an antigen or hapten) in the sample as it mixed with two reagents: the first containing the antigen coated particles, the second containing a fixed and limiting amount of free antibody. Concentrations and amounts of particles, antigen on the particles and of antibody are all selected together such that expected levels of target antigen in the sample will produce significant (and preferably substantially linear) changes in the degree of agglutination of the mixture.

In the present method, the sample, diluent if any and reagent or reagents are all introduced into a chamber capable of being subjected to rotation, such as in a chamber of the rotor of a centrifugal microanalyzer of the types described in U.S. Pat. Nos. 4,226,531 and 4,373,812 and in L. Hills and T. Tiffany, Clin. Chem., vol. 26, pp. 1459-1446 (1980). It will be appreciated that in such a rotor, multiple samples can be simultaneously analyzed in circumferentially spaced chambers, with one or more controls being analyzed simultaneously. As is conventional in centrifugal analysis, the sample and the reagents can be introduced into inner and outer subchambers, with a rapid centrifugation being used to cause the material in the inner chamber to overflow a dam and mix with the material in the outer chamber. Prior to such mixing, the various samples and reagents may be brought to a standard temperature (typically 37° C.). As is conventional for such centrifugal analyzers, the samples are generally rotated sufficiently to continuously mix each sample. It should be appreciated, however, that if the particles, either agglutinated or unagglutinated, have a density essentially equal to the density of the suspending medium, then no degree of centrifugation will cause a gradient of particles to develop in the chamber. It is an important feature of the present invention that the density of the agglutinated particles differ significantly relative to the density of the suspension medium such that, at the centrifugal force applied, migration of particles will occur. In referring to a centrifugal force, it is appreciated that such terminology represents a fiction which nevertheless helps explain the migration of heavier materials outward within a rotating chamber. Encompassed in such terminology is the basic principle described in Stokes' law where the frictional coefficient of a body in a centrifugal field affects its instantaneous velocity and is directly dependent upon that body's radius. Such a situation can be roughly expressed by the following equation:

$$dX/dt = \frac{2 R^2 (D_p - D_m) w^2 X}{9 v}$$

Where $dX/dt$ is the rate of migration of the body; R is the radius of the body (particle), $D_p$ and $D_m$ are the densities of the particle and of the medium, V is the viscosity of the medium, w is the angular velocity (of the rotor) and X is the distance of the body from the center of rotation. As the particles agglutinate, R increases. The term gradient is used to indicate change in concentration of the particles relative to the radial direction within a chamber, it being understood that such gradient can either be an equilibrium gradient established after a given time of reaction and spinning, a kinetic gradient wherein agglutinated particles are constantly moving outward within each chamber, or, most preferably, a reacting kinetic gradient wherein particles are agglutinating during the reaction and thereupon migrate outwardly within the chamber. As indicated in the examples below, however, the density of the suspension medium can be adjusted (with, for example, sucrose being added) so as to closely match the density of agglutinated particles, in which case the migration of agglutinated particles will be greatly inhibited and the selectivity in the present method will be lost.

As indicated in the examples below, however, when the density of the suspending medium ($D_m$) is adjusted (with the addition of sucrose, for example) so that $D_m$ is closely matched to the density of the particles ($D_p$), then the migration of all particles will be severely retarded.

While satisfactory combinations of particle concentration, particle density, suspending medium density and centrifugal force can be adjusted together through no more than routine experimentation, general ranges for each of these parameters are set forth below.

The density of the particles (such is polystyrene latex particles) used in the present Examples is 1.05 g/ml, as determined by the manufacturer for the unconjugated material. The suspending buffer medium has a density ranging from 1.00 (the density of water) to 1.028 g/ml (the density of normal human serum). Densities of the overall suspending medium will be greatly affected by the sample, since sample may contribute one-third to one-half of the total liquid of the incubation mixture.

The magnitude of the centrifugal field exerted during reaction ranges from 33 to 66 G (G being the force of gravity) for the extreme ends of the reaction chamber of the Multistat III microcentrifugal analyzer; the average force at the light path being about 50 G.

Figure 2:
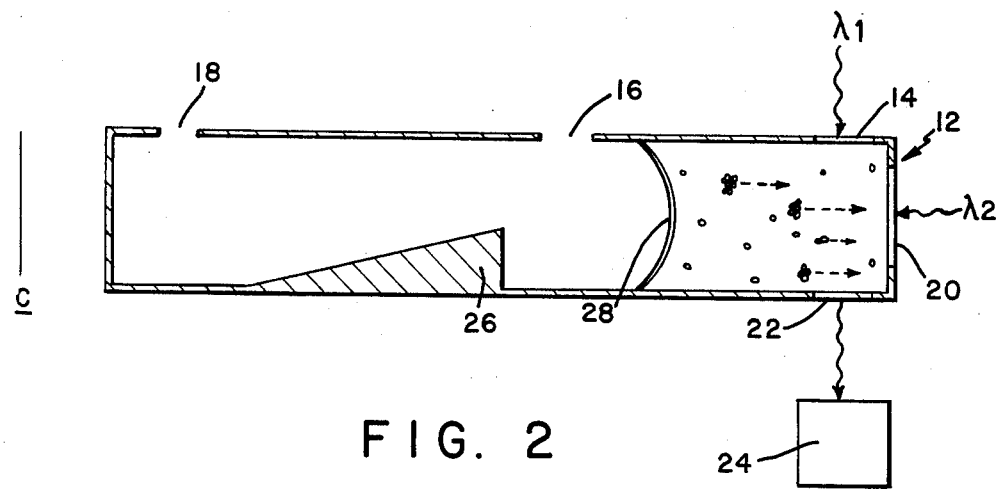
FIG. 2 is an elevational view, in cross section along line 2—2 in FIG. 1, of a reaction chamber of the rotor.

The method of the present invention can be illustrated by reference to FIGS. 1 and 2 showing, respectively, a plan view and an elevational view in cross section of a rotor containing reagents for practice of the present invention.

FIG. 1 shows a plan view of the rotor 10, of the Multistat III ® microcentrifugal analyzer (Instrumentation Laboratory, Lexington, MA.). A plurality of reaction chambers 12 are shown, each with a top optical surface 14, a reagent port 16 and a sample port 18, located progressively inwardly toward the center of rotation C.

FIG. 2 shows a sectional view of one reaction chamber 12, again showing along the top surface the top optical surface 14, the reagent port 16 and the sample port 18. Further shown are the end optical surface 20, bottom optical surface 22 and detector 24, all positioned for measurement of transmitted light (entering through top optical surface 14 and exiting through bottom optical surface 22) or of scattered light (entering through end optical surface 20 and exiting through bottom optical surface 24). The interior area through which such light passes to reach the bottom optical surface 22 (and thereafter passes to detector 24) is referred to herein as the "lightpath" or "locus" at which transmission or light scattering is measured.

In use, reagents (including coated particles) are loaded through reagent port 16 and clinical samples (serum or urine, for example) through sample port 18.

Figure 3A:
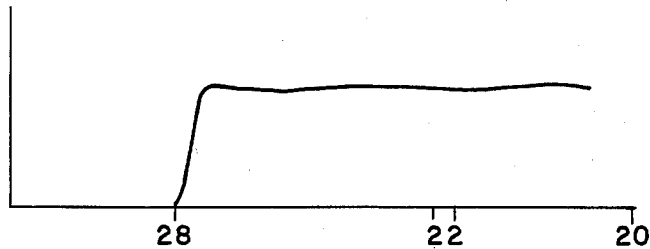
FIGS. 3A-3D are schematic graphic views of the concentration of particles along line 2—2 at various time points in the process of the present invention.

Once all reaction chambers 12 are loaded, the rotor 10 is spun sufficiently fast for the sample to overflow an internal dam 26 and thus mix with reagents in the exterior portion of the reaction chamber 12 (as shown by meniscus 28). Upon initial mixing, it is expected that particles will be uniformly distributed within the liquid phase exterior of the meniscus 28. Thereafter (assuming that agglutination occurs and agglutinated particles migrate outwardly) the distribution of particles between meniscus 28 and end optical surface 20 will become increasingly skewed toward end optical surface 20. This phenomena is schematically shown in FIGS. 3A-3D as follows. FIG. 3A shows the particle distribution upon initial mixing, level from meniscus 28 to past bottom optical surface 22 to end optical surface 20. After some agglutination and centrifugation, the agglutinated particles start to migrate outwardly, increasing the particle concentration through the outer two-thirds of the liquid (see FIG. 3B). Continued agglutination and outward migration caused (FIG. 3C) even greater concentration of particles near end optical surface 20, but now the particle concentration at bottom optical surface 22 is below the initial value of FIG. 3A. Finally (FIG. 3D) essentially all of the agglutinated particles are collected against the outer edge and the concentration of particles at bottom optical surface 22 is at substantial minimum. While the concentration at bottom optical surface 22 may continue to decline very slowly thereafter (due to outward migration of unagglutinated particles), the high rate of change measured between FIGS. 3D and 3C will no longer occur.

Absorbance of light through optical surface 22 during the course of agglutination of said particles may be interpreted in at least one of two methods. In one method, a decrease in the absorbance of light across optical surface 22 over a period of time is measured during the continued outward migration of the particles in the later phases of agglutination, as shown in FIGS. 3C and 3D and described in examples 1-6. Alternatively, the difference in the absorbance of light across optical surface 22 may be measured upon the initial mixing (FIG. 3A) and again when the particle concentration has increased through the outer two-thirds of the liquid (FIG. 3C). Methodology of the second type is described in examples 7-9. The methodologies are shown in parallel in Table 5, below.

EXAMPLE 1

A Multistat II microcentrifugal analyzer and Multistat loader manufactured by Instrumentation Laboratories were used in the following procedure. The geometry is generally as shown in FIGS. 1 and 2.

In each reagent chamber of the Multistat III cuvette rotor was placed 50 μl of a 0.26% (w/w) suspension of HCG-coupled latex 0.58μ (580 nm) diameter obtained from the β-Pregnate slide pregnancy test kit manufactured by Fisher Diagnostics. The latex, as well as all of the reactants used in this procedure, were diluted in 2.5 mg/ml BSA in 0.05M phosphate buffer, pH 7.2 containing 0.15M sodium chloride (PBS).

In the sample chamber of the cuvette rotor was placed 10 μl of a 1:9200 dilution of monoclonal anti-HCG antibody, the same antibody as that used in the PregnaClone kit, also manufactured by Fisher, and 89 μl of a solution containing various amounts of HCG (2nd international standard from the W.H.O.). The reference cuvette contained only water.

The loaded rotor was placed in the Multistat III instrument and internal program for measuring absorbance (light introduced through surface 14 reaching detector 24) as a function of time was recalled. Absorbance was measured at a wavelength of 690 nm. The delay time, between the beginning of the reaction and the first set of absorbance measurements, was set for 10 minutes, with additional sets of absorbance measurements taken at various intervals thereafter (generally every 30 seconds) for up to 30 minutes. The instrument averages each set of absorbance measurements.

The reaction was begun after the rotor compartment had reaced 37° C. by a rapid acceleration of the cuvette rotor, mixing the contents of the sample (inner) and reagent (outer) chambers. After 10 minutes of centrifugation at a constant velocity, absorbance measurements were recorded at 30 second time intervals during continuous centrifugation.

Figure 3B:
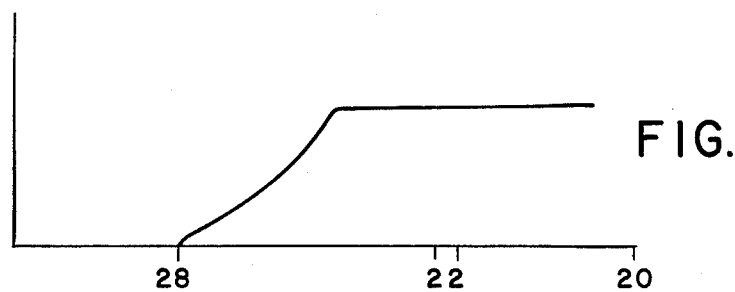
Figure 3C:
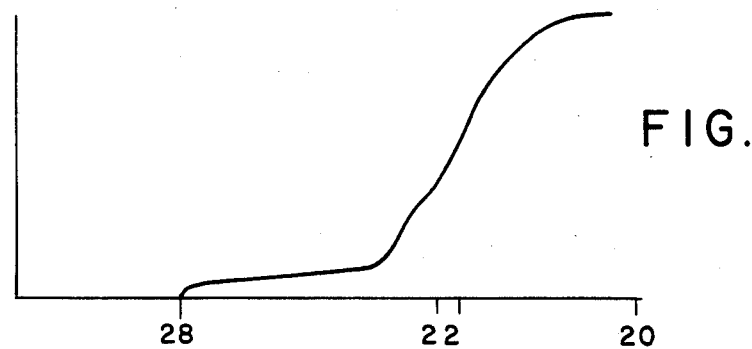
Figure 3D:
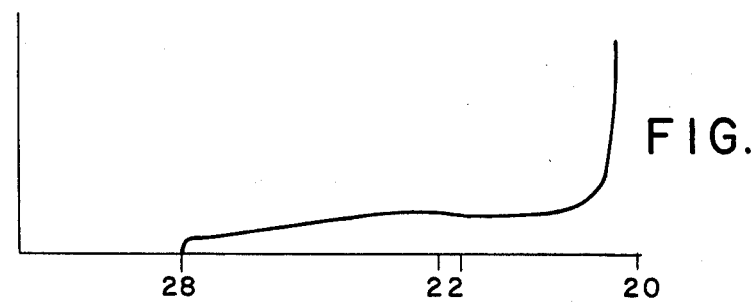

The data resulting from such an experiment are seen as a decreasing absorbance at 690 nm as a function of time with respect to water for each cuvette of the Multistat III rotor as shown in FIG. 3B, 3C and 3D. Decreasing absorbance can be taken as a reduction in particles at the locus of light measurement as more of the particles agglutinate and then migrate further outward than the light path. The rate of absorbance change over the entire time period measured was then described as the slopes of those linear relationships.

The standard curve represented in Table 1 was a secondary plot of the decreasing slopes (i.e., a linear regression) resulting from the inhibition of the latex agglutination of the presence of increasing concentrations of HCG. As little as 1 mIU/ml HCG could be reproducibly detected by this method. The negative values correspond to downward slopes in absorbance over time between 10 and 15 minutes of continuous centrifugation. The units are thousandths of absorbance units per minute.

TABLE 1

| Standard Curve For HCG | |
|---|---|
| HCG Concentration (mIU/ml) | Change of Absorbance At 690 nm Per Minute |
| 0 | −66.5 |
| 2.5 | −56.1 |
| 10 | −51.8 |
| 20 | −43.0 |
| 30 | −35.7 |

TABLE 1-continued

Standard Curve For HCG

| HCG Concentration (mIU/ml) | Change of Absorbance At 690 nm Per Minute |
|---|---|
| 40 | −31.8 |
| 50 | −27.5 |
| 75 | −17.6 |

These values represent, using FIGS. 3A–3D, differences between FIG. 2B and FIG. 2C for various levels of agglutination (more agglutination occurring at lower HCG levels because of the competition mode).

EXAMPLES 2 and 3

Tables 2 and 3 represent standard curves (in thousandths of absorbance units per minute) for HCG using 1:9200 and 1:7700 dilutions of antibody, respectively, and an in-house HCG standard. Experimental procedures and reagents were the same as those described in Example 1 except that the cuvette rotor was loaded by hand.

TABLE 2

STANDARD CURVE FOR HCG USING 1:7700 DILUTION OF ANTIBODY

| HCG Concentration (mIU/ml) | Change of Absorbance At 690 nm Per Minute |
|---|---|
| 0 | −63.1 |
| 1 | −54.7 |
| 5 | −41.5 |
| 10 | −38.0 |
| 20 | −31.7 |
| 30 | −21.5 |
| 40 | −17.5 |
| 50 | −9.5 |
| 75 | −7.5 |

TABLE 3

STANDARD CURVE FOR HCG USING 1:9200 DILUTION OF ANTIBODY

| HCG Concentration (mIU/ml) | Change of Absorbance At 690 nm Per Minute |
|---|---|
| 0 | −29.8 |
| 1 | −22.8 |
| 5 | −18.3 |
| 10 | −14.1 |
| 20 | −11.1 |
| 30 | −7.9 |
| 40 | −6.2 |
| 50 | −5.5 |
| 75 | −4.3 |

The data show a less sensitive standard curve and a greater rate of absorbance change for a greater concentration of antibody.

EXAMPLE 4

Latex used in the PregnaClone tube test manufactured by Fisher Diagnostics was used to establish a standard curve for HCG using the method described in Example 1. A 1:7700 dilution of monoclonal anti-HCG was used.

TABLE 4

STANDARD CURVE FOR HCG USING 0.305 μm DIAMETER LATEX PARTICLE

| CONCENTRATION OF HCG (mIU/ml) | CHANGE OF ABSORBANCE AT 690 nm PER MINUTE (× $10^3$) |
|---|---|
| 0 | −28.8 |
| 2 | −28.7 |
| 4 | −27.8 |
| 6 | −27.7 |
| 8 | −27.2 |
| 10 | −24.7 |
| 15 | −25.3 |
| 20 | −21.0 |
| 30 | −20.2 |

EXAMPLE 5

The concentration of HCG-coupled latex used in the Pregnate slide test manufactured by Fisher Diagnostics was varied to establish its effect on the HCG standard curve. A 1:1900 dilution of monoclonal antibody (from the PregnaClone test) was used. Procedures were the same as those described for example 1, including measurement of absorbance at 690 mm.

Increasing the latex concentration resulted in a greater rate of absorbance change and an increase in sensitivity. Column A, having all negative slopes, represents thousandths of absorbance units per minute over the period from 10 to 15 minutes of continuous centrifugation. Column B, having positive and negative values, represents the difference, in thousandths of absorbance units, between a time after 900 seconds of centrifugation and a time after 3 seconds of centrifugation.

TABLE 5

STANDARD CURVES FOR HCG USING 0.22 μm DIAMETER LATEX AT VARIOUS LATEX CONCENTRATIONS

| CONCENTRATION OF HCG (mIU/ml) | Col. A | Col. B |
|---|---|---|
| 0.05% Latex | | |
| 0 | −19.0 | 98 |
| 25 | −22.2 | 107 |
| 50 | −15.9 | 149 |
| 75 | −11.7 | 249 |
| 0.10% Latex | | |
| 0 | −99.3 | −267 |
| 10 | −100.9 | −220 |
| 25 | −83.6 | −160 |
| 50 | −46.6 | 120 |
| 75 | −21.3 | 347 |
| 0.15% Latex | | |
| 0 | −196.4 | −670 |
| 10 | −181.9 | −653 |
| 25 | −167.8 | −525 |
| 50 | −62.2 | 58 |
| 75 | −11.0 | 504 |

EXAMPLE 6

Latex agglutination was followed by the change in absorbance with time during centrifugation on the Multistat III. Procedures and reagents were exactly as those described for Example 1 in the presence or absence of 6% sucrose as shown in Table 6. No free HCG is present.

The same reagents were used to follow agglutination by measuring the change in absorbance at 690 nm on a Perkin-Elmer model 320 spectrophotometer as seen in Table 7.

TABLE 6

The effect of sucrose on the decrease in absorbance on the Multistat III.

| Time of Reaction | Absorbance At 690 nm | |
|---|---|---|
| (minutes) | With Sucrose | Without Sucrose |
| 0 | 2.287 | 2.073 |
| 2 | 2.254 | 1.897 |
| 4 | 2.218 | 1.686 |
| 6 | 2.182 | 1.478 |
| 8 | 2.150 | 1.291 |
| 10 | 2.092 | 1.132 |
| 12 | 2.041 | 0.996 |
| 14 | 1.995 | 0.891 |
| 16 | 1.945 | 0.805 |

TABLE 7

The effect of sucrose on the decrease in absorbance on the spectrophotometer.

| Time of Reaction | Absorbance at 690 nm | |
|---|---|---|
| (minutes) | with sucrose | without sucrose |
| 10 | 0.759 | 0.801 |
| 15 | 0.748 | 0.782 |
| 20 | 0.732 | 0.762 |
| 30 | 0.701 | 0.726 |
| 40 | 0.674 | 0.692 |
| 50 | 0.651 | 0.667 |
| 65 | 0.627 | |
| 70 | | 0.622 |

Because of differences (e.g., path length) between these two experiments, the raw data of Table 6 should not be compared directly to the raw data of Table 7. The significant factor is the slope (with or without sucrose) in each table.

While the presence of sucrose greatly inhibited the decrease in absorbance observed using continual centrifugation on the Multistat III, sucrose had no effect on the agglutination reaction itself as measured without centrifugation by spectrophotometer. These data indicate that centrifugal force (effective only when sucrose is absent) is mainly responsible for the decrease in absorbance observed on the Multistat III resulting from the rapid clearance of latex aggregates from suspension at the locus of the light path.

EXAMPLE 7

A Multistat III microcentrifugal analyzer was used as in Example 1 except that the reaction and measurement conditions were changed as follows. Components from an HCG Pregnate# Latex beads were diluted 1/50 in buffer with 0.1M glycine, 0.3M NaCl, 1% bovine serum albumin and 0.05% Triton X-100, pH 9.0. Of this diluted reagent, 150 μl was added to each of the reagent chambers of the Multistat III cuvette rotor. Antiserum was diluted 1/5, and 25 μl placed in the sample chambers of the rotor. Urine samples with various known HCG contents (25 μl) were also placed in sample chambers.

Absorbance was measured at 380 nm. The delay time between the beginning of the reaction and first set of absorbance measurement was 3 seconds, with additional sets of absorbance measurements taken at various intervals thereafter for 15.8 minutes.

The standard curve represented in Table 8 with centrifugation presents the final absorbance reading minus the initial reading (and thus corresponds to the final column in Table 5). The change in absorbance is positive during the reaction time period.

The same reagents were used to follow agglutination by measuring the change in absorbance at 380 nm on a Bausch & Lomb Spectronic 2000 spectrophotometer. The data presented in Table 8 for reaction without centrifugation has been adjusted according to Beer's law for differences in cuvette path length between the Multistat III cuvette and the spectrophotometer cuvette. Centrifugation increases the change in absorbance for agglutinated samples.

TABLE 8

Standard Curve for HCG using 0.22 μm Diameter Latex Beads

| Concentration of HCG | Change of Absorbance at 380 nm (× 10³) | |
|---|---|---|
| mIU/ml | with centrifugation | without centrifugation |
| 800 | 3.5 | 3.8 |
| 400 | 18.0 | 14.0 |
| 200 | 36.7 | 20.8 |
| 80 | 49.0 | 31.5 |
| 40 | 69.5 | 38.3 |
| 8 | 75.5 | 42.3 |
| 4 | 80.2 | 46.0 |

EXAMPLE 8

Fisher anti-CRP latex reagent diluted 1/30 in PBS (150 μl) was placed in the reagent chambers of the Multistat II cuvette rotor. Various dilutions of CRP-containing serum were placed in the sample chambers (30 μl). The reaction was performed as in Example 7, except that the final absorbance measurement was 15 minutes after the initial reading and readings were taken at 340 nm.

Figure 4:
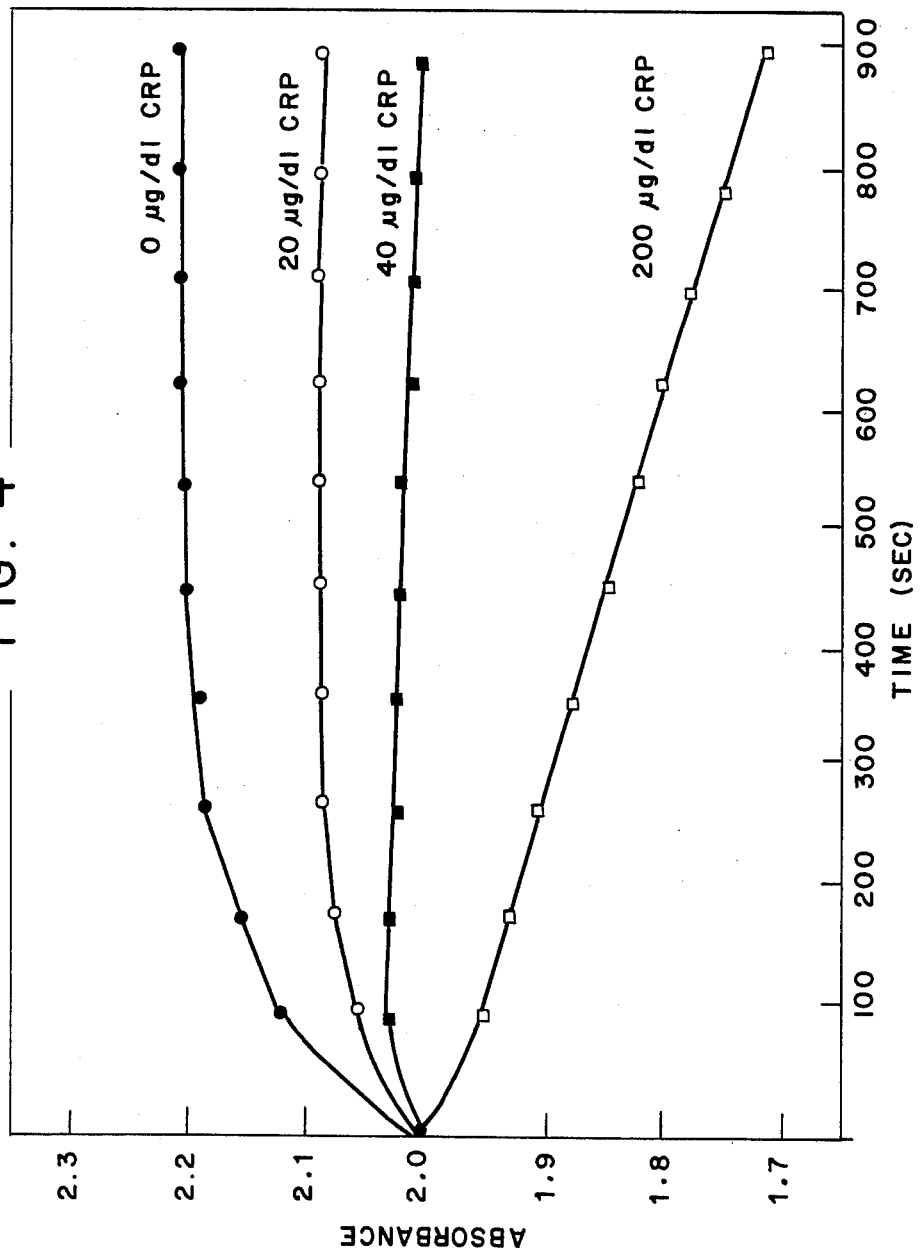
FIG. 4 is a graphic view of data from Example 8.

FIG. 4 shows the time course of reactions with 0, 20, 40 and 200 μg/dl CRP samples. The pattern of absorbance with time varies with antigen concentration. Table 9 shows the differences between final and initial absorbance values for a set of CRP standards. Increased concentration corresponds to increased agglutination.

TABLE 9

Standard Curve for C-reactive Protein Using anti-CRP Coated Latex Beads (.428 μm)

| Concentration CRP (μg/dl) | Change of Absorbance at 340 nm (× 10³) |
|---|---|
| 0 | 192 |
| 5 | 175 |
| 10 | 145 |
| 20 | 70 |
| 40 | −15 |
| 80 | −114 |
| 120 | −196 |
| 160 | −260 |
| 200 | −290 |

What is claimed is:

1. A method for the determination of a target binding pair member in a sample which comprises:
   (a) admixing the sample with a reagent containing stably suspended particles, the particles being coated with a member selected from the group consisting of binding pair members complementary to the target binding pair member and binding pair members competitive with the target binding pair member, the mixture further containing complementary binding pair member when the coated member is competitive;
   (b) subjecting the mixture during reaction between binding pair members to a centrifugal force sufficient to differentially change the concentration of particles in the mixture at a locus relative to the total concentration of particles in the mixture, the rate of such change being a function of the degree of agglutination of the particles;

(c) measuring the light transmission or scattering at the locus at a plurality of points of time during reaction and application of centrifugal force; and (d) comparing the change in light measurement over time at the locus for the mixture containing sample with changes in light measurement over time at the locus for mixtures containing standard samples of known concentration of the target pair member.

2. The method of claim 1 wherein the suspended particles are latex particles a diameter about 0.05 to about 2.0 microns (about 50 to 2000 nm) and the suspension medium is aqueous and is less dense than agglutinated particles.

3. The method of claim 2 wherein the latex particles are polystyrene.

4. The method of claim 1 wherein the mixture is subjected to centrifugal force in a rotor and the locus is spaced from the exterior of the rotor, whereby the concentration of particles decrease in concentration at the locus over time as a function of the rate of formation of agglutinated particles.

5. The method of claim 1 wherein the target binding pair member is an antigen and particles are coated with antibody.

6. The method of claim 1 wherein the target binding pair member is an antigen or hapten, the particles are coated with a competitive antigen or hapten and the mixture further contains a limiting quantity of antibody binding specifically to the target binding pair member to the competitive antigen.

7. The method of claim 1 wherein the measuring step (c) comprises exposing the sample at a locus to light and measuring the light transmitted through the mixture at the locus.

8. The method of claim 7 wherein the transmitted light is substantially monochromatic.

* * * * *